US00PP18387P3

(12) United States Plant Patent
Garrison et al.

(10) Patent No.: US PP18,387 P3
(45) Date of Patent: Jan. 1, 2008

(54) **HOMOZYGOUS MALE *ASPARAGUS* PLANT NAMED 'NJ22-34'**

(50) Latin Name: *Asparagus officinalis*
Varietal Denomination: NJ22-34

(75) Inventors: Stephen A. Garrison, Pittsgrove, NJ (US); Chee-kok Chin, Holmdel, NJ (US); John J. Kinelski, Princeton, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 11/431,329

(22) Filed: May 10, 2006

(65) Prior Publication Data

US 2007/0266466 P1 Nov. 15, 2007

(51) Int. Cl.
*A01H 5/00* (2006.01)

(52) U.S. Cl. ..... Plt./260

(58) Field of Classification Search ..... Plt./260
See application file for complete search history.

*Primary Examiner*—Kent Bell
*Assistant Examiner*—Annette H Para
(74) *Attorney, Agent, or Firm*—James A. Lucas; Driggs, Hogg & Fry Co., L.P.A.

(57) ABSTRACT

A new and distinct *asparagus* (*Asparagus officinalis* Linn.) plant denoted 'NJ22-34' which is homozygous for male sex gene was developed through extensive breeding and selection. *Asparagus* hybrid 'NJ22-34' has many desirable traits including homogenous in male genes, good resistance to rust (*Puccinia asparagi*) and good field tolerance to *asparagus* root rot (*Fusarium oxysporum*) and *asparagus* crown rot (*Fusarium moniliforme*). Because 'NJ22-34' is a homozygous-male plant all its F1 progenies will be male plants. This invention relates to the plant and plant parts of 'NJ22-34'. The invention further relates to hybrid *asparagus* seeds and plants produced by crossing *asparagus* plant 'NJ22-34' with another *asparagus* plant.

1 Drawing Sheet

Latin name of the genus and species: The Latin name is *Asparagus officinalis*.

Variety denomination: The varietal denomination is 'NJ22-34'.

CROSS REFERENCE TO RELATED APPLICATIONS

This application is related to co-pending plant patent application Ser. No. 11/431,187 entitled GENOTYPE OF *ASPARAGUS* PLANT NJ 44P which is owned by the assignee of the present invention and is filed currently herewith.

BACKGROUND OF THE INVENTION

For an *asparagus* plant to be commercially viable and profitable, good yield is essential. It is well known that *asparagus* is susceptible to a number of diseases. Among the most devastating are rust caused by *Puccinia asparagi* d.c., (Kahn et al. 1952), crown rot caused by *Fusarium oxysporum* and root rot caused by f. *Proliferatum* (syn=f. Moniliforme) (Johnston et al., 1979; Guerrero et al., 1999). Of course, the presence of these diseases aversely impacts the yields and therefore the profitability of the product. Accordingly, resistance to these diseases is essential to commercial success.

BRIEF SUMMARY OF THE INVENTION

This invention relates to a new and distinct homozygous-male *asparagus* plant designated as 'NJ22-34'. Plant 'NJ22-34' possesses several desirable traits including vigorous growth habit, resistance to rust (*Puccinia asparagi*), and good field tolerance to root and crown rot (*Fusarium oxysporum*) and (*Fusarium mondiforme*), respectively, as compared to its progenies.

BRIEF SUMMARY OF THE DRAWINGS

The color notations in our Data Summary have been selected by us from observations as compared with the Munsell Limit Color Cascade, Munsell Color. It should be mentioned that foliage color of *asparagus* could be affected by many factors including plant nutrition, temperature, humidity and the density of growth. Therefore, the color characteristics of this new variety should be determined with reference to the observations described herein, rather than from this illustration alone. Furthermore, the coloration is not considered to be a distinguishing feature of this new variety.

DETAILED DESCRIPTION OF THE INVENTION

Figure 1:
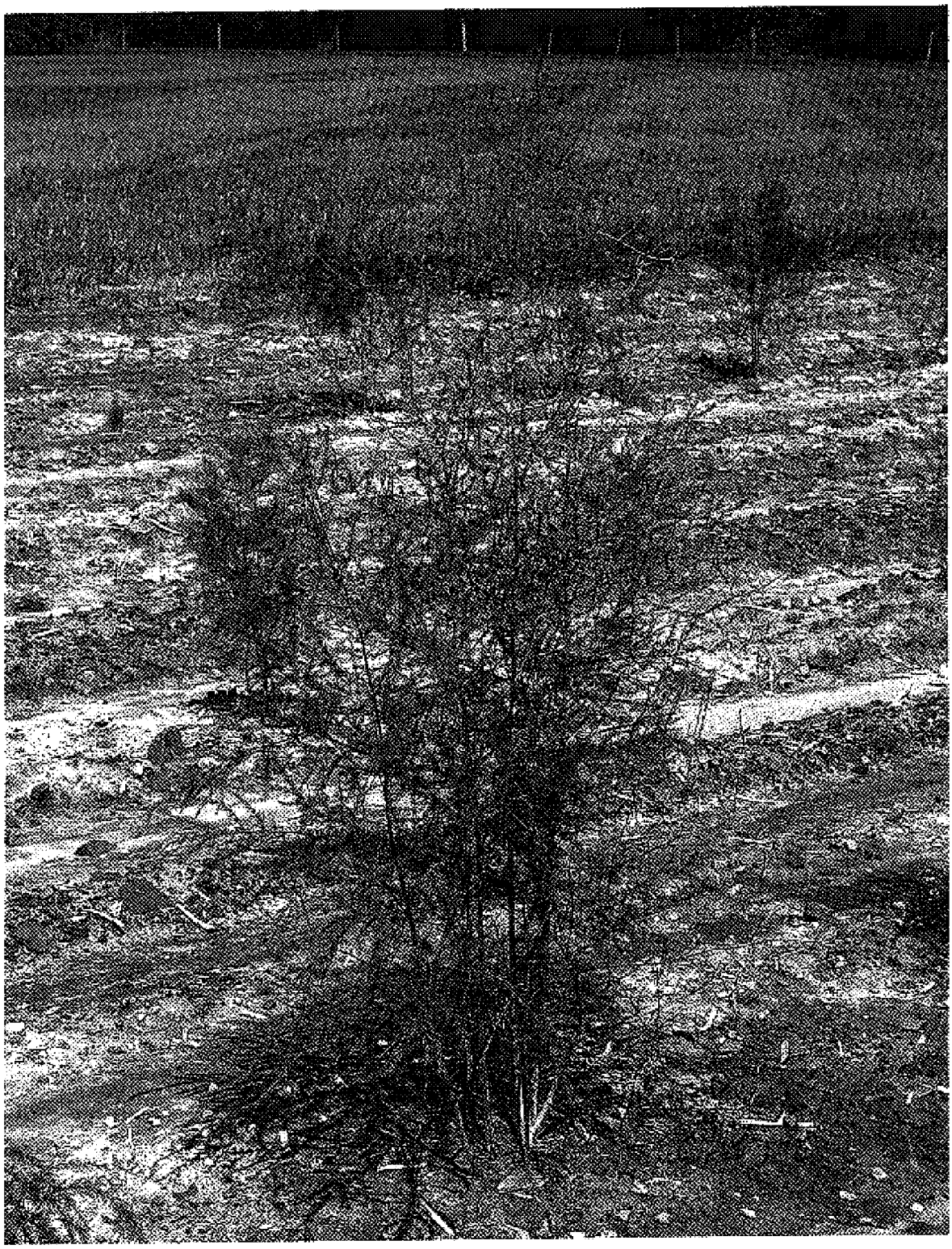
FIG. 1 shows in color a typical planting of 'NJ22-34' as it appears in a field under normal conditions.

An extensive program of *asparagus* plant development, carried out at a cultivated area in the vicinity of Bridgeton, N.J. and New Brunswick, N.J. has resulted in the development of the *asparagus* hybrid plant 'NJ22-34' with many desirable traits. 'NJ22-34' was produced by self-fertilization of an andromonoecious male plant known as *Asparagus* Plant No. 22 (U.S. Pat. No. PP4,999). Asexual reproduction of 'NJ22-34' has been conducted via tissue culture in a laboratory in New Brunswick, N.J.

*Asparagus* (*Asparagus officinalis* Linn.) is a dioecious species with individual plants being either male or female in sex. In addition to differences in morphology "cultivars"

may also differ in local adaptation, yield, disease resistance, and longevity. Desirable cultivars are developed by crossing of elite male and female parents. Both male and female parents transmit traits such as disease resistance, yield, and spear morphology to their progenies. 'NJ22-34' is produced by self-fertilization of an andromonoecious plant 'NJ22'. The *asparagus* plant 'NJ22-34' is a homozygous male. All of the F1 progenies produced by crossing any female with 'NJ22-34' will be males.

Good yields is essential for profitability. Yield of *asparagus* may vary significantly among genotypes. In tests carried out in different locations, hybrids of crosses of different females and 'NJ22-34' produced higher yield than hybrids of crosses of different females and previously patented *asparagus* plant 22-8 (U.S. Pat. No. PP5,549, Ellison).

The following table shows that the progenies of 'NJ22-34' out yield the progenies of NJ22-8, which is the parent of Jersey Giant (U.S. Pat. No. PP5,551) and Jersey Knight (U.S. Pat. No. PP6,624), two highly popular *asparagus* varieties cultivated around world today.

TABLE 1

| Crosses | Name | Yield, LB/A |
|---|---|---|
| NJ56 × NJ22-34 | NJ854 (US PP16140) | 4881 |
| G27 × NJ22-34 | Not named | 4424 |
| NJ277C × NJ22-34 | Not named | 4215 |
| G27 × NJ22-8 | Jersey Gem (US PP6970) | 3673 |
| NJ362M × NJ22-34 | Not named | 3645 |
| NJ56 × NJ22-8 | Jersey Giant | 3595 |
| NJ277C × NJ22-8 | Jersey Knight | 3278 |
| NJ362M × NJ22-8 | Jersey General (US PP6965) | 3155 |

*Asparagus* can be clonally propagated by crown division. Crown is the structure where shoots and roots join together. Division or separation at the crown area will allow the propagation of *asparagus*. It has been observed that 'NJ22-34' plants propagated by crown division have similar morphological appearance and possess the same desirable characteristics as the original 'NJ22-34'.

*Asparagus* can also be clonally propagated by tissue culture. An *asparagus* shoot tip or meristem when cultured on appropriate nutrient medium and appropriate conditions can grown, develop, and regenerated into a plant. Also, *asparagus* plant part such as a spear segment when cultured on appropriate nutrient medium and appropriate conditions can grow, develop, and regenerate into *asparagus* plant. Such plant can be efficiently divided and multiplied in appropriate nutrient medium. The 'NJ22-34' plant propagated by various tissue culture techniques possesses and retain the same desirable characteristics as the original 'NJ22-34' plant.

This invention also includes hybrids produced by crossing a female *asparagus* plant with 'NJ22-34'. When crossed with different female plants, *asparagus* 'NJ22-34' produced only male hybrids. 'NJ22-34' can transmit its desirable traits including vigorous growth habit, resistance to rust (*Puccinia asparagi*) good field tolerance to root and crown rot (*Fusarium oxysporum*) and (*Fusarium mondiforme*) to its progenies.

Morphological data has been accumulated that distinguishes *asparagus* plant NJ22-34 from other *asparagus* varieties that developed internally, as well as *asparagus* plants that are known and available commercially in the markets.

BOTANICAL DESCRIPTION

The data (averages from 3 clones) are assembled in the following table:
*ASPARAGUS* PLANT: 'NJ22-34'

TABLE 2

Stalk data:

Number of nodes below first branch: 29.3.
Distance from crown to first branch: 55.8 cm.
Number of branches: 53.
Distance between first and last branch: 118.96 cm.
Internode length between branches: 2.24 cm.
Number of cladophyll nodes beyond last branch: 31.67.
Length beyond last branch: 13.33 cm.
Largest stalk diameter: 15 mm.
Mean diameter of three largest stalks: 13.33 mm.
Number of stalks: 38.
Mature stalks color, bloom removed: Color No. 22-11.
Typical and observed branch color: Color No. 19-11.

Flower

Typical number per cluster: 2.
Tepal - 6 per flower.
Apex outer surface margin Color No. 23-6.
Apex inner surface margin Color No. 25-5.
Apex outer surface middle (vertical) area Color No. 47-5.
Apex inner surface middle (vertical) area Color No. 23-5.
Base outer surface margin Color No. 23-8.
Base inner surface margin Color No. 25-3.
Base outer surface middle (vertical) area Color No. 47-8.
Base inner surface middle (vertical) area Color No. 23-8.
Shape - elliptic, average 7.8 mm long. 3.2 mm wide at mid point, slightly wider towards apex, fused in lower third into a tubular corolla, imbricate in bud; apex obtuse; base cunneate; margin entire.
Flower length: 7.8 mm.
Flower width at midpoint: 3.2 mm.
Pedicel: filiform: length 16 mm; no bract.

Cladophyll

Average number per node: 7.8.
Shape: linear, filiform, needle-like; apex acute; base cuneate, margin - entire;
Color - 20-11.
Average length of cladophylls on first node: 25 mm.
Average width of cladophylls on first node: 0.8 mm.

Leaves

Main stem leaves scale-like, triangular, average 13 mm long, 12 mm wide at base, membranous: apex acuminate; base truncate; margin hyaline; Color - 28-9 abaxial; 28:8 adaxial.
Terminal branch leaves scale-like, triangular, average 5 mm long, 3 mm wide at base, membranous; apex acuminate; base truncate; margin erose, hyaline. Color: 28-8 abaxial; 28-7 adaxial.

Reproductive organs

Stamens - 6 in number, each stamen fused to middle of inner side of a tepal.
Filaments - filiform, straight, slightly wider at base 4.5 mm long; Anthers elliptic, longitudinally dehiscent, introse to slightly latorose, base sagittate, apex obtuse with small acuminate tip.

What is claimed is:

1. A new and distinct *asparagus* plant 'NJ22-34', which is homozygous for male sex gene as herein shown and described.

* * * * *